(12) United States Patent
Zhang et al.

(10) Patent No.: US 8,684,942 B2
(45) Date of Patent: Apr. 1, 2014

(54) SYSTEM FOR CARDIAC IMPAIRMENT DETECTION BASED ON SIGNAL REGULARITY

(75) Inventors: Hongxuan Zhang, Palatine, IL (US); Steve D Quam, Carpentersville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/352,380

(22) Filed: Jan. 18, 2012

(65) Prior Publication Data

US 2012/0302903 A1 Nov. 29, 2012

Related U.S. Application Data

(60) Provisional application No. 61/489,704, filed on May 25, 2011.

(51) Int. Cl.
*A61B 5/00* (2006.01)

(52) U.S. Cl.
USPC .......................................... 600/508

(58) Field of Classification Search
None
See application file for complete search history.

(56) References Cited

U.S. PATENT DOCUMENTS

| | | |
|---|---|---|
| 4,681,117 A | 7/1987 | Brodman et al. |
| 4,798,211 A | 1/1989 | Goor et al. |
| 4,924,875 A | 5/1990 | Chamoun |
| 4,930,075 A | 5/1990 | Kortas |
| 5,010,888 A | 4/1991 | Jadvar et al. |
| 5,054,496 A | 10/1991 | Wen et al. |
| 5,159,932 A | 11/1992 | Zanetti et al. |
| 5,365,426 A | 11/1994 | Siegel et al. |
| 6,024,705 A | 2/2000 | Schlager et al. |
| 6,038,469 A | 3/2000 | Karlsson et al. |
| 6,112,116 A | 8/2000 | Fischell et al. |
| 6,339,720 B1 | 1/2002 | Anzellini et al. |
| 6,368,284 B1 | 4/2002 | Bardy |
| 6,424,860 B1 | 7/2002 | Karlsson et al. |
| 6,468,263 B1 | 10/2002 | Fischell et al. |
| 6,501,983 B1 | 12/2002 | Natarajan et al. |
| 6,882,883 B2 | 4/2005 | Condie et al. |
| 7,072,708 B1 | 7/2006 | Andersen et al. |
| 7,181,268 B2 | 2/2007 | Sheldon et al. |

(Continued)

OTHER PUBLICATIONS

Bretthorst GL. Bayesian Spectrum Analysis and Parameter Estimation. In: Berger J, Fienberg S, Gani J, Krickeberg K, Singer B (Eds.). Lecture Notes in Statistics. Springer-Verlag, New York, N.Y. 1988.*

(Continued)

*Primary Examiner* — Brian T Gedeon
*Assistant Examiner* — Ankit Tejani
(74) *Attorney, Agent, or Firm* — Brennan K. Bradley (57) ABSTRACT

A system for heart performance characterization and abnormality detection comprises an input processor and a signal processor. The input processor receives first sampled data representing a first signal portion of a heart activity related signal and second sampled data representing a second signal portion of a heart activity related signal. The signal processor determines distribution data associated with degree of similarity between the first and second signal portions by determining a difference between (a) values derived by applying a first function to mean adjusted sampled values of the first signal portion and (b) values derived by applying a second function to mean adjusted sampled values of the second signal portion. In response to the determined distribution data, the signal processor initiates generation of a message associated with the degree of similarity between the first and second signal portions.

19 Claims, 9 Drawing Sheets

(56) References Cited

U.S. PATENT DOCUMENTS

| | | |
|---|---|---|
| 7,181,269 B1 | 2/2007 | Kroll |
| 7,225,015 B1 | 5/2007 | Xiaoyi et al. |
| 7,231,244 B2 | 6/2007 | Laitio et al. |
| 7,266,410 B2 | 9/2007 | Chen |
| 7,277,745 B2 | 10/2007 | Natarajan et al. |
| 7,299,087 B2 | 11/2007 | Bardy |
| 7,361,473 B2 | 4/2008 | Valkirs et al. |
| 7,415,307 B2 | 8/2008 | Sharma et al. |
| 7,456,179 B2 | 11/2008 | Ghanbari et al. |
| 7,542,794 B1 | 6/2009 | Zhang et al. |
| 7,643,872 B2 | 1/2010 | Xiaoyi et al. |
| 7,797,036 B2 | 9/2010 | Zhang et al. |
| 7,860,559 B2 | 12/2010 | Fischell et al. |
| 2006/0235319 A1* | 10/2006 | Belohlavek et al. .......... 600/509 |
| 2009/0112106 A1 | 4/2009 | Zhang |
| 2009/0281441 A1 | 11/2009 | Zhang et al. |
| 2010/0094125 A1* | 4/2010 | Younge et al. ................ 600/424 |
| 2010/0094147 A1* | 4/2010 | Inan et al. .................... 600/500 |
| 2010/0174205 A1* | 7/2010 | Wegerif ........................ 600/515 |
| 2011/0087121 A1 | 4/2011 | Zhang et al. |
| 2011/0166618 A1 | 7/2011 | Zhang |
| 2011/0245669 A1 | 10/2011 | Zhang |

OTHER PUBLICATIONS

S Abbound, RJ Cohen, A Selwyn, P Ganz, D. Sadeh and PL Friedman, "Detection of transient myocardial ischemia by computer analysis of standard and signal-averaged high-frequency electrocardiograms in patients undergoing percutaneous transluminal coronary angioplasty", Circulation, vol. 76, p. 585-596, Sep. 1987.

Stuart E. Sheifer, MD, Teri A Manolio, MD, PHD; and Bernard J. Gersh, MS, CHB, DPHIL, "Unrecognized Myocardial Infarction", Annals of Internal Medicine, Nov. 6, 2001, vol. 135, Issue 9, pp. 801-811.

\* cited by examiner

SYSTEM FOR CARDIAC IMPAIRMENT DETECTION BASED ON SIGNAL REGULARITY

This is a non-provisional application of provisional application Ser. No. 61/489,704 filed May 25, 2011, by H. Zhang et al.

FIELD OF THE INVENTION

This invention concerns a system for heart performance characterization and abnormality detection involving determining distribution data associated with degree of similarity between first and second signal portions of a heart activity related signal.

BACKGROUND OF THE INVENTION

Myocardial ischemia and infarction analysis and detection within ventricular tissue, for example, is used in the management of cardiac disorders and irregularities, which are caused by a lack of blood and oxygen, in heart tissue. Usually, surface ECG signal analysis based on waveform morphology and time domain parameters is utilized for myocardial ischemia and infarction detection and characterization, such as by determination of ST segment or T wave changes (repolarization). However known systems fail to provide a comprehensive quantitative method for myocardial status detection and characterization, such as for severity characterization of an ongoing myocardial ischemia event with chest pain and discomfort. Additionally, known systems for cardiac ischemia and infarction identification and analysis based on ECG signals are typically subjective and need extensive expertise for accurate pathology interpretation and proper cardiac rhythm management.

Coronary Artery Disease (CAD) and heart-related problems and cardiac arrhythmias are severe frequently fatal conditions. A 12-lead electrocardiogram (ECG) and multi-channel intra-cardiac electrogram (ICEG) comprise a diagnostic reference standard used for evaluating cardiac rhythm and events. Known waveform morphology and time domain parameter analysis, such as of a P wave, QRS complex, ST segment and T wave, are used for cardiac arrhythmia monitoring and identification, e.g. of atrial fibrillation (AF), myocardial ischemia (MI) and ventricular tachycardia/fibrillation (VT/VF), for example. However, waveform morphology and time domain parameter analysis are sometimes subjective and time-consuming, and require extensive expertise and clinical experience for accurate interpretation and proper cardiac rhythm management.

Cardiac electrophysiological activities and signals (ECG and ICEG signals) are time varying and known signal analysis typically fails to localize a precise malfunction and identify its severity and an associated trend of cardiac events (e.g. of myocardial ischemia and infarction), such as cardiac pathology irregularity stages and arrhythmia occurrence. Known clinical diagnosis of myocardial ischemia and infarction detection and characterization are based on ST segment voltage deviation for ischemia event detection (e.g. 0.1 mV elevation is a clinical standard for myocardial ischemia (MI) detection). However this standard only works for surface ECG signals, NOT for intra-cardiac electrograms (ICEG signals) and ST segment (voltage) deviation fails to indicate myocardial ischemia severity.

Known systems for myocardial ischemia and infarction analysis typically need a benign signal as a baseline for threshold determination of events and lack reliability, stability and accuracy, especially in emergency cases. Known methods for MI analysis focus on an event which is more qualitative involving detection and evaluation of MI occurrence and lack a capability for quantitative characterization of MI severity. Furthermore, known ischemia event detection systems may cause a false alarm due to reliance on single parameter analysis such as measurement of magnitude of an ST segment. Known medical applications also need improved accuracy and capability for timely detection and characterization of an MI event, which can be used in an ICD (Implantable Cardiac Defibrillator) or a portable system in cardiac applications, such as Holster monitoring. A system according to invention principles addresses these deficiencies and related problems.

SUMMARY OF THE INVENTION

A system analyzes cardiac electrophysiological signals using ventricular depolarization signal regularity to detect and characterize cardiac arrhythmia and heart tissue functions by calculation of joint mutual distribution density and bilateral mutual regularity between ventricular and atrial depolarization electrophysiological responses of signals within the same heart beat. A system for heart performance characterization and abnormality detection comprises an input processor and a signal processor. The input processor receives first sampled data representing a first signal portion of a heart activity related signal and second sampled data representing a second signal portion of a heart activity related signal. The signal processor determines distribution data associated with degree of similarity between the first and second signal portions by determining a difference between (a) values derived by applying a first function to mean adjusted sampled values of the first signal portion and (b) values derived by applying a second function to mean adjusted sampled values of the second signal portion. In response to the determined distribution data, the signal processor initiates generation of a message associated with the degree of similarity between the first and second signal portions.

DETAILED DESCRIPTION OF THE INVENTION

A system analyzes cardiac electrophysiological signals (including surface ECG signals and intra-cardiac electrograms, ICEG signals) using ventricular depolarization signal regularity to detect and characterize cardiac arrhythmia and heart tissue functions. The ventricular depolarization regularity is quantified and analyzed by calculation of joint mutual distribution density and bilateral mutual regularity between ventricular and atrial depolarization electrophysiological responses of signals within the same heart beat. The system analysis is usable in real time monitoring and analysis of myocardial tissue pathology (especially ventricular ischemia and infarction), such as in implantable devices, for example. The system improves identification of cardiac disorders, differentiates cardiac arrhythmias, characterizes pathological severity, predicts life-threatening events, and supports determination of drug delivery effects.

The system provides single beat signal analysis to estimate ventricular myocardial tissue variation and functionality changes and in one embodiment uses cardiac signal bilateral mutual regularity based cardiac arrhythmia analysis, particularly myocardial ischemia and infarction analysis. The system employs a mutual distribution density and mutual bilateral regularity analysis of ventricular and atrial depolarization procedures for cardiac signal analysis. Known methods for myocardial ischemia event detection (particularly ventricular ischemia) rely on repolarization procedure related changes, such as ST segment and T wave morphology changes. The system in contrast uses depolarization signals from a ventricle for ischemia and infarction characterization and uses a combination of different derived parameters for diagnosing both the depolarization and repolarization procedures, including timing, frequency and energy change related parameters.

During ventricular ischemia, various portions of heart muscle receive less oxygen which can ultimately lead to irreversible scarring and necrosis of the muscle tissue (myocardial infarction), reducing the efficiency with which the heart can pump blood to the rest of the body and possibly leading to fatal cardiac arrhythmias. Myocardial ischemia or infarction reduces blood flow to regions of the heart, where cells respond by altering action potential. The changes in individual cells manifest in change in local electrograms during depolarization and repolarization, reducing signal energy (hyperkalemia or anoxia) or creating multi-phasic waveforms (decoupling). These abnormal behaviors in relatively small regions of the heart, lumped together with the rest of the heart, cause notches and slurs of small amplitude superimposed on a largely normal electrograms, both surface ECG signals and intra-cardiac electrograms. The system also provides data variance and statistical characteristics such as parameter ratios indicative of atrial versus ventricle depolarization and repolarization functions using time varying signals (ECG and ICEG signals). The system uses nonlinear and non-uniform data sampling and construction.

Figure 1:
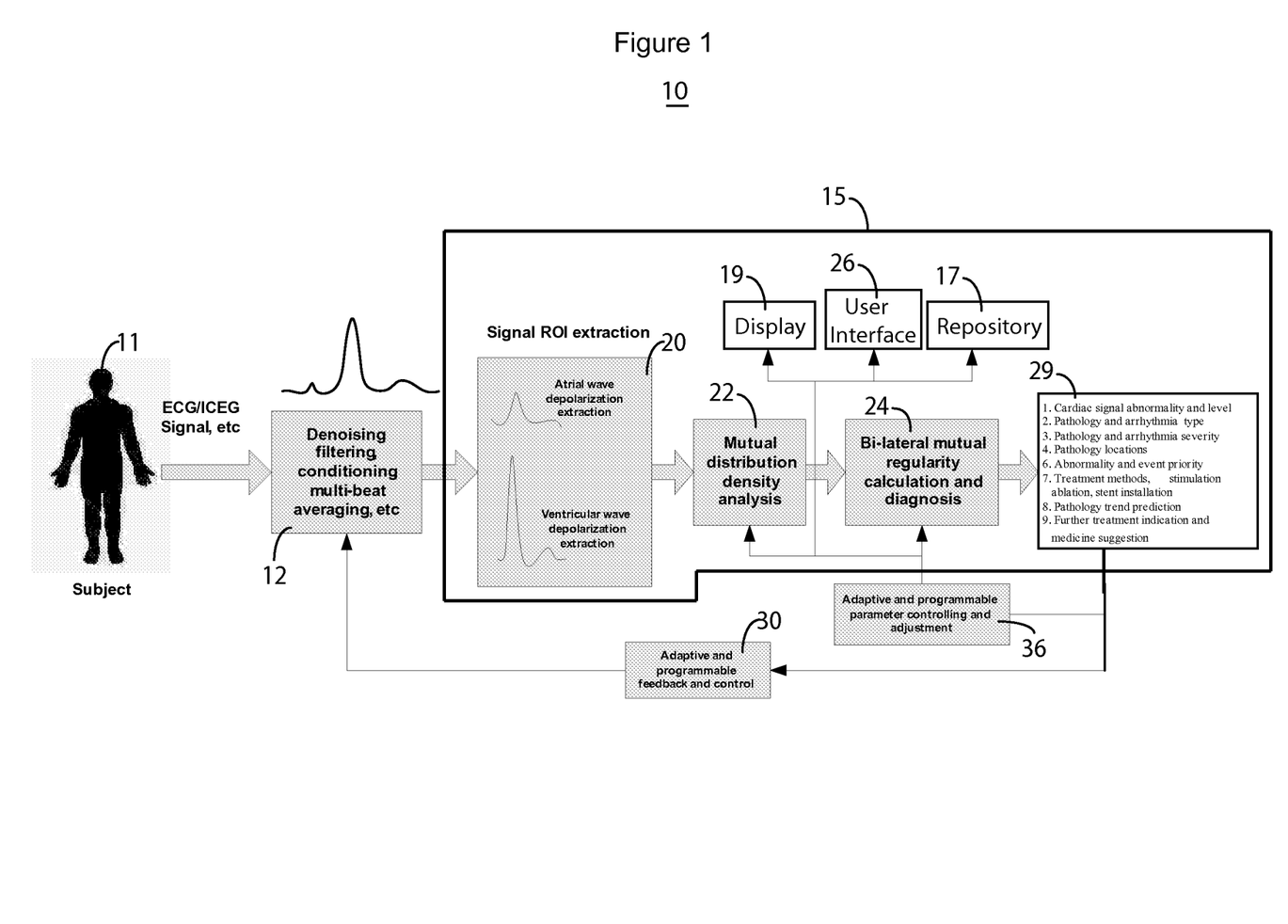
FIG. 1 shows a system for heart performance characterization and abnormality detection, according to invention principles.

FIG. 1 shows system 10 for heart performance characterization and abnormality detection involving ventricular depolarization medical signal sampling and acquisition for myocardial ischemia and infarction detection, for example. Input processor 12 receives and processes an ECG (and ICEG) signal from patient 11 by de-noising, filtering, conditioning and buffering the received signal. Input processor 12 adaptively performs multi-heart cycle averaging on the de-noised, filtered and buffered received signal based on determined signal noise level, signal bandwidth, and data indicating type of anatomical region of interest (ROI) and analysis being performed. Atrial depolarization and ventricular depolarization signals are detected and extracted and mutual distribution density and Bi-lateral mutual regularity are calculated. Extraction unit 20 in signal processor 15 identifies atrial and ventricular waveform portions and identifies P, Q, R, S, T and U wave ECG signal portions and the P, Q, R, S, T and U points themselves by detecting peaks of an ECG (and ICEG) waveform within received sampled data by synchronization of a heart electrical activity waveform and peak detection of a wave using a known peak detector and by identifying peaks of other waves by segmenting the signal represented by the sampled data into windows where the waves are expected and identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of a signal as determined by the peak detector. The baseline of the signal may comprise a zero voltage level if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

Signal processor 15 unit 22 receives from unit 20 first sampled data representing a first signal portion (e.g. an Atrial depolarization portion) of a heart activity related signal and second sampled data representing a second signal portion (e.g. a Ventricular depolarization portion) of a heart activity related signal. Processor 15 calculation unit 24 determines distribution data such as a bilateral mutual regularity calculation associated with degree of similarity between the first and second signal portions by determining a difference between (a) values derived by applying a first function to mean adjusted sampled values of the first signal portion and (b) values derived by applying a second function to mean adjusted sampled values of the second signal portion. The first function and the second function comprise probability density functions. Unit 29 in processor 15 derives output parameters indicating cardiac signal abnormality level, pathology and arrhythmia type and severity, pathology tissue location, an abnormality and event priority, treatment methods such as ablation, stimulation and use of a stent. Pathology trend identification and suggested candidate treatment and medication.

System 10 advantageously uses mutual bilateral regularity analysis between atrial and ventricular depolarization electrophysiological activities in the same cardiac heart beat signal to diagnose electrophysiological activities of the heart tissue and functional status. Most myocardial action potentials within a heart occur in two procedures, depolarization and repolarization, within the four chambers. The action potentials from the heart cells and tissues accumulate and construct the heart electrograms, which are known as ECG (from body surface) and intra-cardiac electrograms. Hence different portions of an electrogram represent the cardiac activities of a corresponding cardiac area and tissue. For example, a P wave represents action potential and activities of atrial tissue and muscles while a QRS complex represents transition of cardiac excitation from atrium to ventricle. Furthermore, action potentials, even in the same ECG signal portion (e.g. the QRS complex) such as QR portion and RS portion, may represent different kinds of procedure. For ischemia and infarction monitoring and event characterization, a precise portion of electrophysiological signals is extracted and analyzed by processor 15.

In response to the determined distribution data, processor 15 initiates generation of a message associated with the degree of similarity between the first and second signal portions. Further in response to the determined distribution data and derived output parameters unit 30 provides adaptive programmable feedback control of de-noising, filtering, buffering and averaging of the received signal by input processor 12. In addition, in response to the determined distribution data and derived output parameters, unit 36 provides adaptive programmable parameter control and adjustment of signal processor 15 including determining ECG signal portion selection, distribution data function selection and type of bilateral mutual regularity calculation and associated analysis.

System 10 comprises at least one computer system, workstation, server or other processing device comprising signal processor 15 including repository 17, display 19 and user interface 26 (e.g. keyboard, mouse, touchscreen, voice recognition device) for user data and command entry into system 10 via a graphical user interface (GUI) presented on display 19. Repository of data 17 comprises determined distribution data, selectable predetermined functions, ECG signal data and derived output parameters for a particular patient specific calculation distribution data.

System 10 uses a ventricular depolarization signal to track, capture and characterize myocardial arrhythmias and malfunctions. Myocardial ischemia in a ventricle (especially the left ventricle) may cause significant reduction of coronary blood flow which may result in serious chest pain, discomfort, and fatality. Usually a ventricular depolarization process is significantly affected and distorted. This is because coronary blood flow reduction affects a ventricular myocardial cell, especially action potentials, and a ventricular depolarization signal statistical distribution advantageously determined by processor 15 is modified, distorted and changed as a result. However, atrial depolarization is relatively stable and less distorted since most ischemia events are associated with left ventricle tissue. Hence, a calculated distribution comparison between atrial and ventricular depolarization is advantageously used to accurately capture and characterize ventricular ischemia events and pathology at an early stage. The system performs comparisons and mutual bilateral parameter calculation between atrial and ventricular depolarization of the same heart beat signal (or same averaged heart beat signal), but uses a different signal portion (for example, a P wave portion for atrial activity and RT wave portion for ventricular activity), to monitor and detect myocardial events, quantify and characterize event severity and type, suggest treatment and drug delivery timing and priorities, without using a baseline or predetermined benign signal selection and analysis.

Figure 2A:
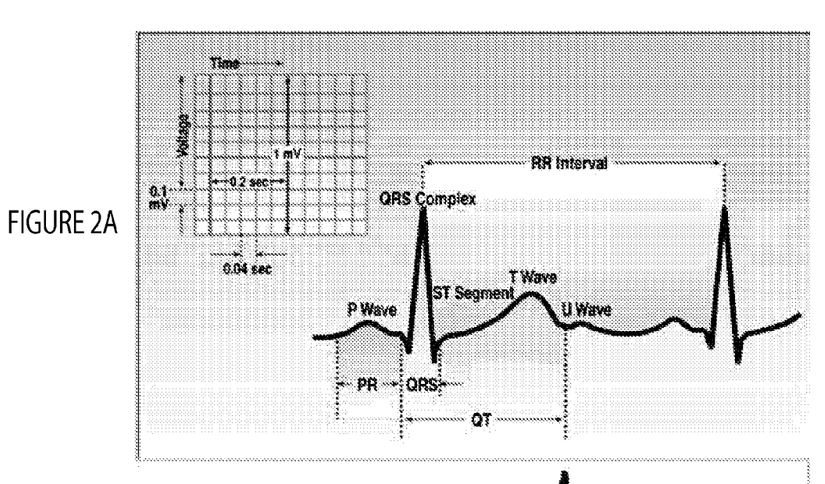
FIGS. 2A and 2B illustrates a conduction procedure in a heart, showing both atrial and ventricular depolarization signals and an ischemia event.
Figure 2B:
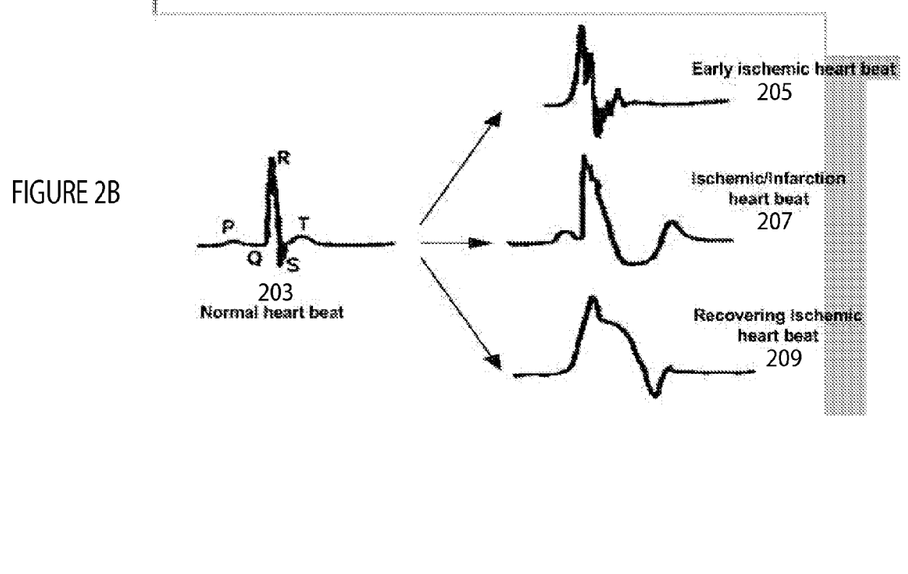

FIGS. 2A and 2B illustrates a conduction procedure in a heart, showing both atrial and ventricular depolarization signals and an ischemia event. The Figures show electrophysiological signal morphologies and waveform shapes of a surface ECG signal, indicating RR wave interval, P wave and QRS complex. FIG. 2A shows an action potential signal, including voltage and time range, e.g. a 0.1 mV threshold indicating ischemia events for ST segment analysis. FIG. 2B shows a procedure indicating a short ischemia event, from normal heart beat 203 to an early ischemic heart beat 205 to ischemia/infarction (lack of blood) heart beat 207 and to recovering ischemic heart beat 209. The heart beat waveforms show ventricular depolarization signal portion RT, QRS complex portion and ST segment changes during a myocardial ischemia event. There may be multiple signal deviations and changes which potentially indicate ischemia and infarction (especially for non-symptomatic myocardial ischemia cases and small ST segment changes in myocardial ischemia cases). Processor 15 detects changes including ST segment change, RS and RT portion change. An RT ROI signal portion is defined from R wave peak to early onset time of a T wave and is used as a ventricular depolarization portion. An RT ROI signal may be an 80-100 mS window from an R wave peak time. Further, a P wave (atrial electrophysiological signal) may be used as a signal distortion baseline.

Typically known clinical methods for myocardial ischemia and infarction detection and diagnosis are based on ST segment elevation (such as above a 0.1 mV change standard level). However these known methods need clinical experience and expertise to interpret signals and lack ischemic severity quantification. Also known myocardial ischemia analysis is restricted to using surface ECG signals and not other (e.g. ICEG) electrophysiological signals. In some clinical cases, an ST segment may fail to show a substantial change, especially in a non-symptomatic case.

Figure 3A:
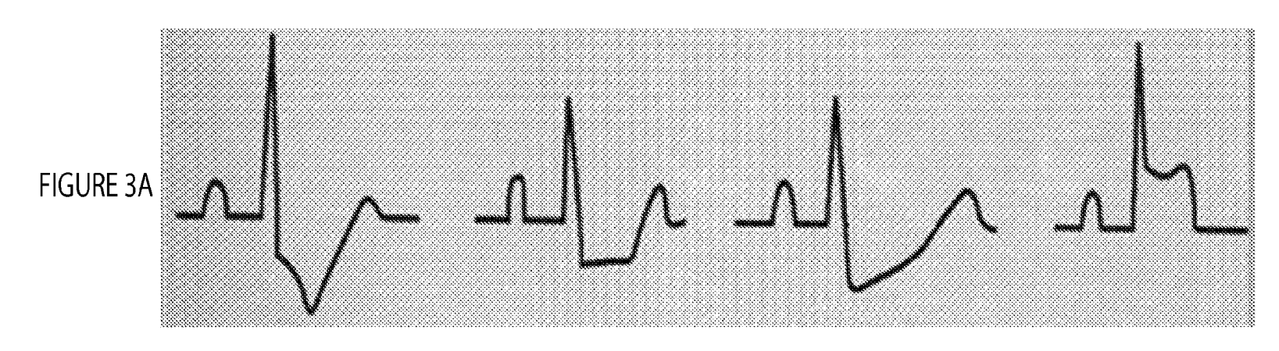
FIGS. 3A and 3B shows different kinds of myocardial ischemia cases and corresponding electrophysiological signal and waveform morphologies that known systems can and cannot detect, respectively.
Figure 3B:
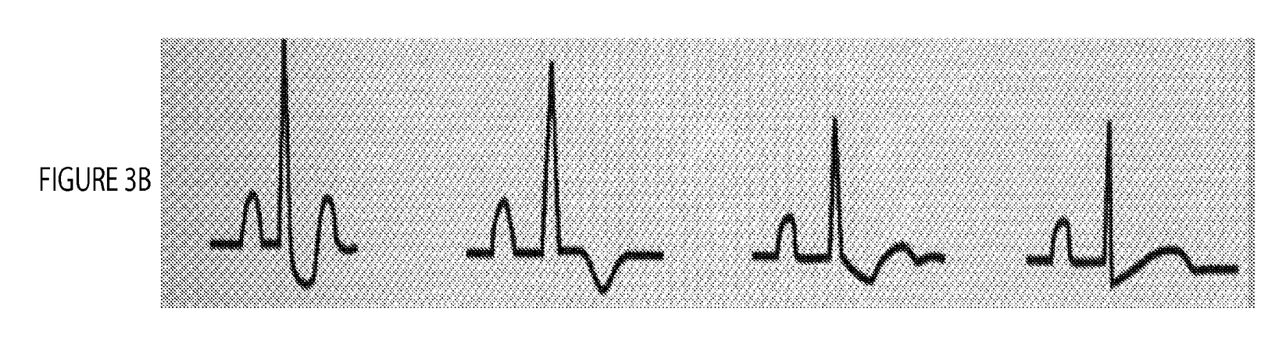

FIGS. 3A and 3B shows different kinds of myocardial ischemia cases and corresponding electrophysiological signal and waveform morphologies that known systems can and cannot detect. FIG. 3A shows ischemia events that can be detected by known systems from the shown electrophysiological signals. FIG. 3B shows ischemia events that typically cannot be detected by known systems from the shown electrophysiological signals. In FIG. 3B, changes in the QRS and T waves, for example, can be utilized for myocardial ischemia (MI) and infarction characterization. In MI events, atrial depolarization portions and signals (e.g. a P wave) are usually stable and without substantial change or distortion while an RT signal portion (including RS ventricular depolarization and ST segment portion) may change due to ventricular myocardial muscle contraction distortion due to lack of blood flow in coronary arteries.

In one embodiment, system 10 performs a joint analysis by comparing a stable atrial depolarization signal (P wave) and ventricular depolarization signal (RT portion) in a mutual combination calculation. This enables detection of a myocardial ischemia pathology event and determination of severity, location (e.g. in a left ventricle) and event timing within a heart cycle. System 10 enables characterization of myocardial ischemia and infarction events without need to use a pre-selected baseline heart beat or benign signal for comparison.

Figure 4:
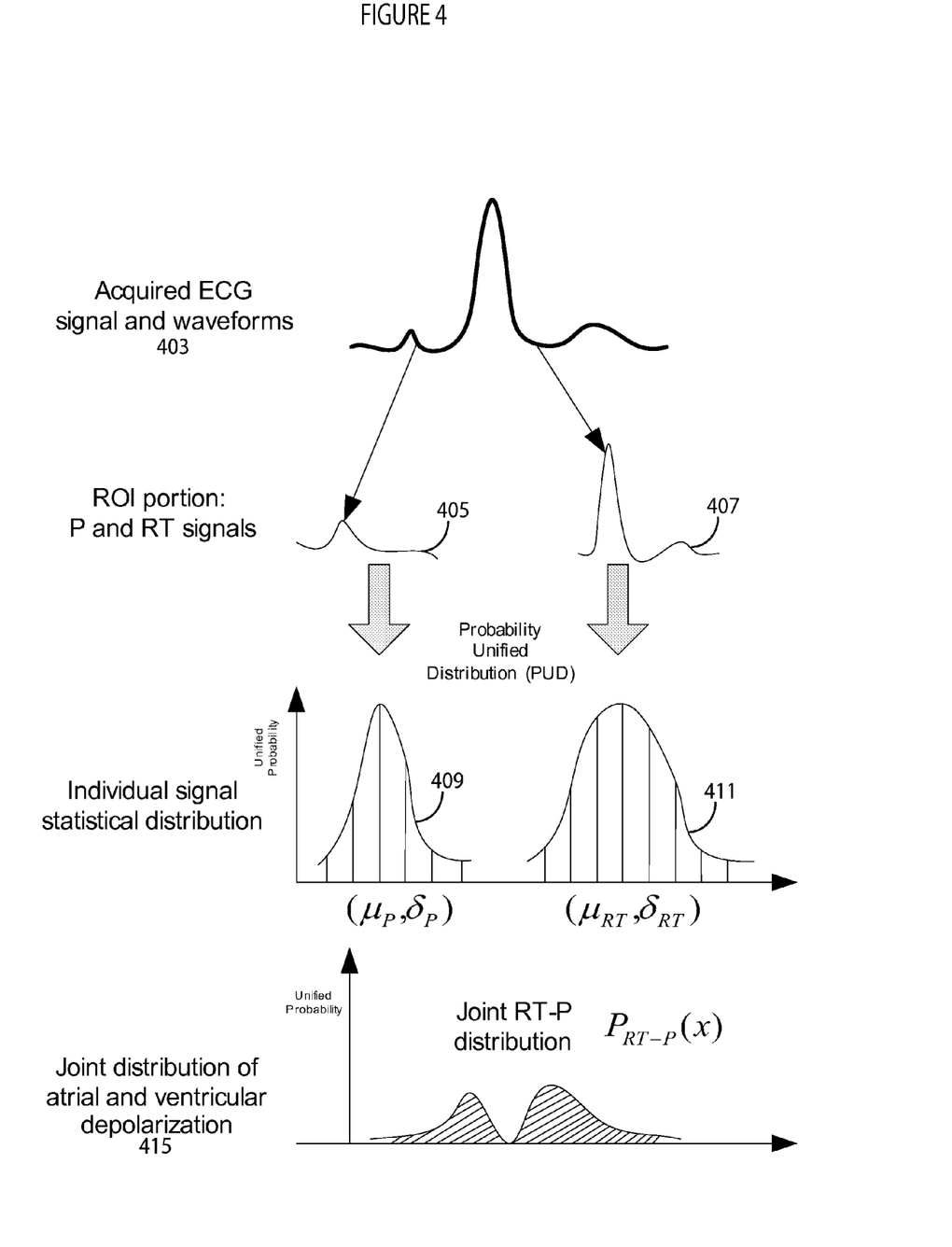
FIG. 4 shows determination of a joint mutual statistical distribution of RT-P portions of an ECG signal, for atrial versus ventricular depolarization analysis, according to invention principles.

FIG. 4 shows determination of a joint mutual statistical distribution 415 of RT 407 and P 405 portions of ECG signal 403, for atrial versus ventricular depolarization analysis. Different portions of a heart signal from different heart regions are used in combination in analysis, involving a mutual statistical distribution calculation. FIG. 4 illustrates determination of a joint mutual statistical distribution of RT and P portions, for atrial and ventricular depolarization. The joint mutual statistical distribution calculation includes heart beat signal recognition and extraction, including signal filtering and conditioning, RR wave detection, P wave detection and ST wave detection. A heart beat signal may be a single heart cycle signal or multiple heart cycles and the signal may be an averaged signal of multiple heart cycles derived using a shifting calculation window involving a shifting window size which may be variable to reduce noise and based on clinical application requirements (such as a window size of 1 to 20 heart beats).

The joint mutual statistical distribution calculation includes signal portion extraction of a ROI including a P wave in extracting atrial and ventricular depolarization signal portions. The system determines individual statistical distribution data for P wave and RT portions, such as mean value μ and standard deviation δ as illustrated for distributions 409 and 411. The system determines a probability distribution unification parameter which matches atrial and ventricular statistical distributions by determination of a joint mutual distribution between atrial and ventricular ROI statistical signals. Different methods may be used to determine a joint mutual distribution. In one embodiment a joint mutual statistical distribution comprises a differential statistical distribution between an atrial and ventricular individual distribution (with a mean value removed from the distribution). So the joint mutual distribution density is a probability distribution function of the mutual distribution $P_{RT-P}(x)$.

FIG. 4 shows calculation of an atrial and ventricular mutual density function. Mutual distribution density is calculated in one embodiment using, for example, the function, $$p_{RT-P}(x) = p_{RT}(x-\mu_{RT}) - p_P(x-\mu_P)$$

where, x is a data point in the distribution, p(•) is the distribution probability function, $p_{RT}(•)$ and $p_P(•)$ are a unified statistical distribution (having mean value μ) for an RT portion and P portion of a signal.

A bilateral mutual regularity function is calculated in one embodiment for example using, $$\text{Bilateral mutual regularity}(BMR) = \frac{|\mu_{RT} - \mu_P|}{|\delta_{RT} - \delta_P|} \cdot \left[ -\sum_{x \in \Omega} p_{RT-P}(x) \cdot \log p_{RT-P}(x) \right]$$

where $\mu_{RT}$ and $\mu_P$ are the mean value of the RT and P wave signal portions and data, $\delta_{RT}$ and $\delta_P$ are the standard deviation of the RT and P wave portions, $p_{RT-P}(x)$ is a mutual joint distribution density function, Ω is the data space of the mutual distribution for an atrial and ventricular combined statistical distribution signal.

Figure 5:
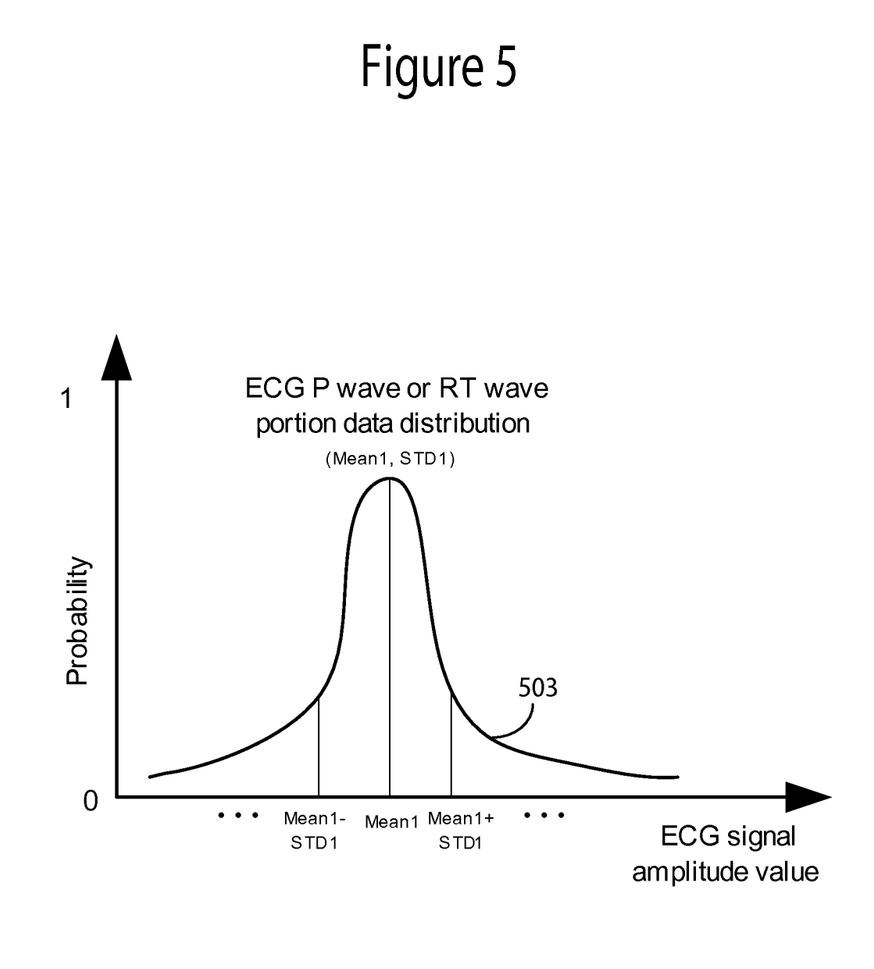
FIG. 5 shows a probability density function of ECG signal amplitude values, according to invention principles.

A Probability Density Function (PDF) of a continuous random variable is a function which can be integrated to obtain a probability that the random variable takes a value in a given interval. A PDF is used to find a point of a Distribution curve. There are different kinds of probability density function of different kinds of data distribution. A Continuous Probability Density Function of a Normal Distribution is called a Gaussian Function. FIG. 5 shows a probability density function of ECG signal amplitude values. The ECG signal data distribution 503 is shown (e.g., of a P wave or RT wave ECG portion) comprising probability (0 to 1 scale) versus ECG amplitude. Lower probability means lower likelihood of occurrence of an ECG signal amplitude. Based on the shape of an ECG portion data distribution probability density function, a signal parameter is calculated for use in diagnosis. Different kinds of distribution density function are adaptively selected by the system for different kinds of signal processing in response to data identifying a clinical procedure being performed. In one embodiment a uniform or normal distribution is utilized to derive statistical parameters and to derive a combined joint mutual distribution density function. In addition to a probability density function, other functions may be utilized in a bilateral mutual regularity calculation including, a frequency spectrum function, a high order statistical index function (such as a bi-spectral function) and an intrinsic characteristic and signal distribution function of the data set. The bilateral mutual regularity reflects similarity in energy and distortion of different heart beat signal portions, such as of a P wave and RT segment.

Figure 6:
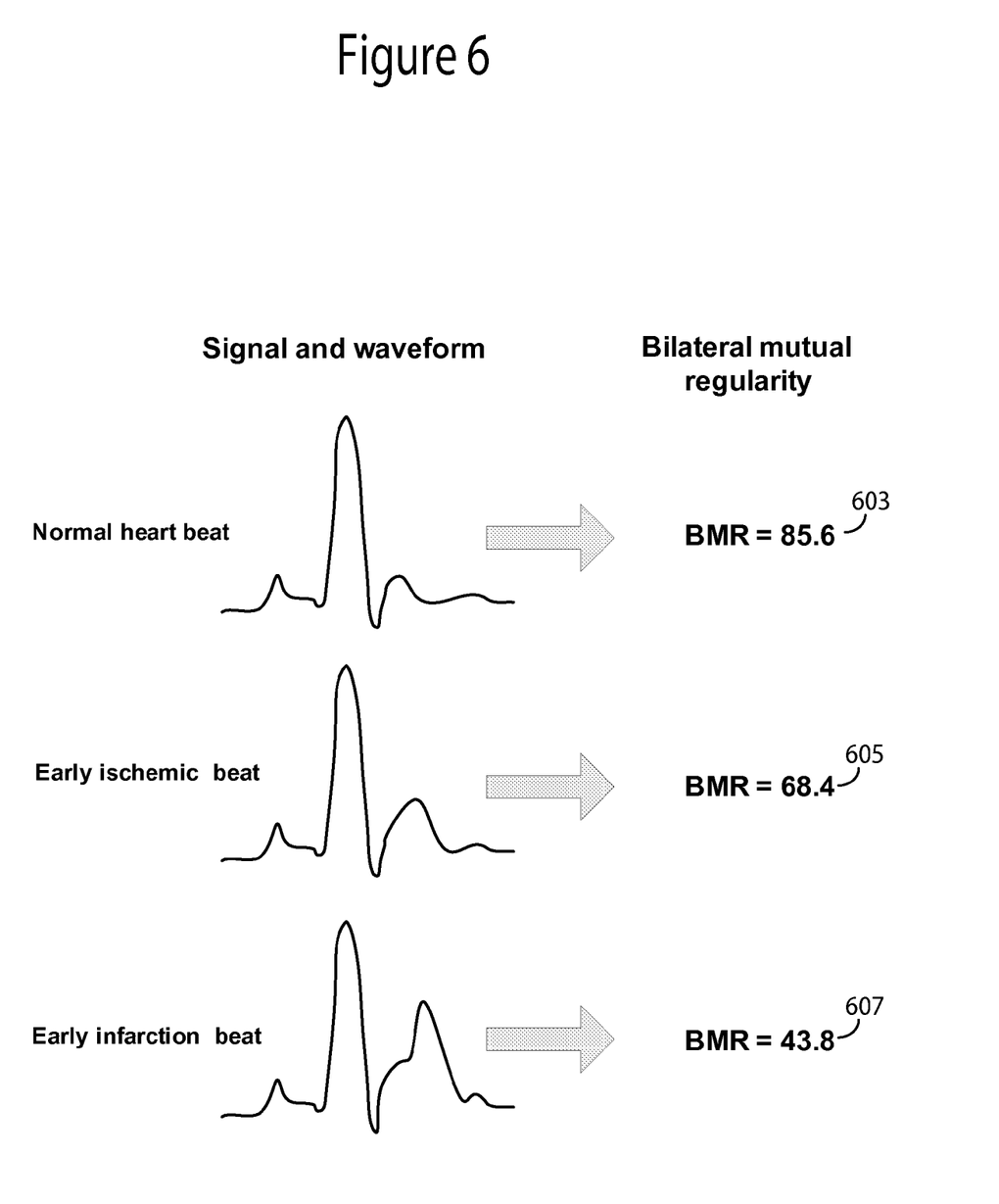
FIG. 6 shows calculated bilateral mutual regularity values for normal, ischemia, and early infarction stages, according to invention principles.

FIG. 6 shows calculated bilateral mutual regularity values for normal, ischemia, and early infarction stages. The corresponding bilateral mutual regularity values of normal 603, ischemia 605, and early infarction 607 stage heart beats are calculated as 85.6, 68.4 and 43.8 respectively. Hence by using a bilateral mutual regularity value, different kinds of ischemic events and myocardial pathologies are differentiated, detected, and characterized. Similarly, a bilateral mutual regularity value is also used to characterize and quantify myocardial ischemia and infarction severity, to facilitate treatment. The bilateral mutual regularity calculation uses different signal portions for comparison comprising, in one embodiment, different portions of different cardiac signals and in another embodiment different portions of a single cycle of the same heart activity signal. The bilateral mutual regularity calculation may also be used between different kinds of signals, such as between an ECG signal and a blood pressure signal to identify different kinds of small statistical changes within signals.

Figure 7:
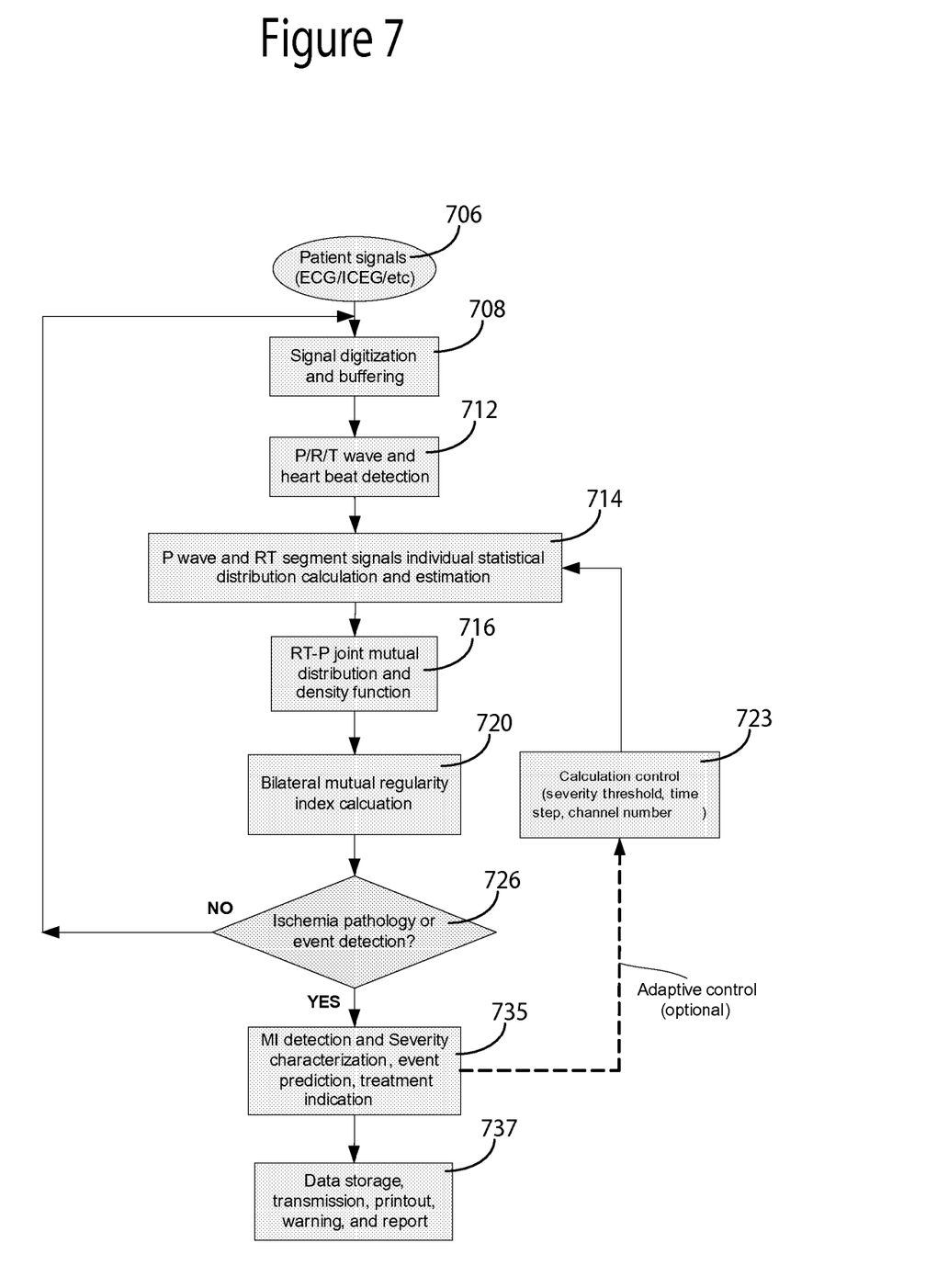
FIG. 7 shows a flowchart of real time bilateral mutual regularity analysis for ischemia detection and characterization, according to invention principles.

FIG. 7 shows a flowchart of a process performed by system 10 (FIG. 1) for real time bilateral mutual regularity analysis for ischemia detection and characterization. Input processor 12 buffers, filters, conditions and digitizes an ECG (or ICEG) signal in step 708 received in step 706. Processor 12 in step 708 filters the received signal data using a filter adaptively selected in response to data indicating clinical application to remove patient movement and respiratory artifacts as well as power line noise. In step 712, signal processor 15 detects P wave, Q wave, R wave, T wave, S wave, U wave and RT segments of the filtered received signal data by detecting peaks within the received data using a known peak detector and by segmenting a signal represented by the received data into windows where the waves are expected and by identifying the peaks within the windows. Processor 15 also detects a heart beat cycle such as between R peaks. The start point of a wave, for example, is identified by a variety of known different methods. In one method a wave start point comprises where the signal crosses a baseline of the signal (in a predetermined wave window, for example). Alternatively, a wave start point may comprise a peak or valley of signal.

In step 714, processor 15 calculates a Probability Density Function (PDF) of data in P wave and RT segments, for example, including mean and standard deviation values of the data values of the individual segments. Signal processor 15 in step 716 calculates RT-P joint mutual distribution density functions and in step 720 calculates a bilateral mutual regularity value. If signal processor 15 in step 726, compares the calculated bilateral mutual regularity value with predetermined thresholds and ranges to identify a medical condition such as ischemia or another abnormality, processor 15 in step 735 uses mapping information, associating ranges of RT-P calculated joint mutual distribution density values and values derived from the RT-P joint mutual distribution density values with corresponding medical conditions in determining severity, type and location of a cardiac condition.

The mapping information associates the thresholds and ranges with particular patient demographic characteristics and with corresponding medical conditions. Processor 15 uses patient demographic data including at least one of, age weight, gender and height in comparing an RT-P joint mutual distribution density value with the thresholds and ranges and in step 737 generates an alert message indicating a potential medical condition and stores data indicating the identified condition and associated calculated parameters in repository 17. Processor 15 in step 723 adaptively and automatically selects a signal channel of a multi-channel ECG system, adjusts a time window as well as window shift step and selects the selected portions and ROI of a filtered signal and adjusts a threshold employed by processor 15 to improve medical condition detection. If signal processor 15 in step 726 does not identify a medical condition, the process is repeated from step 708. Processor 15 in step 737 stores in repository 17 calculated values, detected conditions and associated thresholds and ranges used in condition determination and generates a warning message indicating an identified condition. A warning threshold for a specific patient and pathology is predetermined and stored in repository 17 in one embodiment.

Bilateral mutual regularity based ischemia detection and analysis is used to identify cardiac disorders, differentiate cardiac arrhythmias, characterize pathological severity, predict life-threatening events, and facilitate treatment, such as drug delivery and long term cardiac care. The detection and analysis method may be used by a bedside cardiac monitoring system or portable patient cardiac function monitoring and analysis system, such as a Holster Monitor, for example. A joint mutual distribution density function and bilateral mutual regularity are used for myocardial ischemia and infarction event and pathology detection and characterization.

Figure 8:
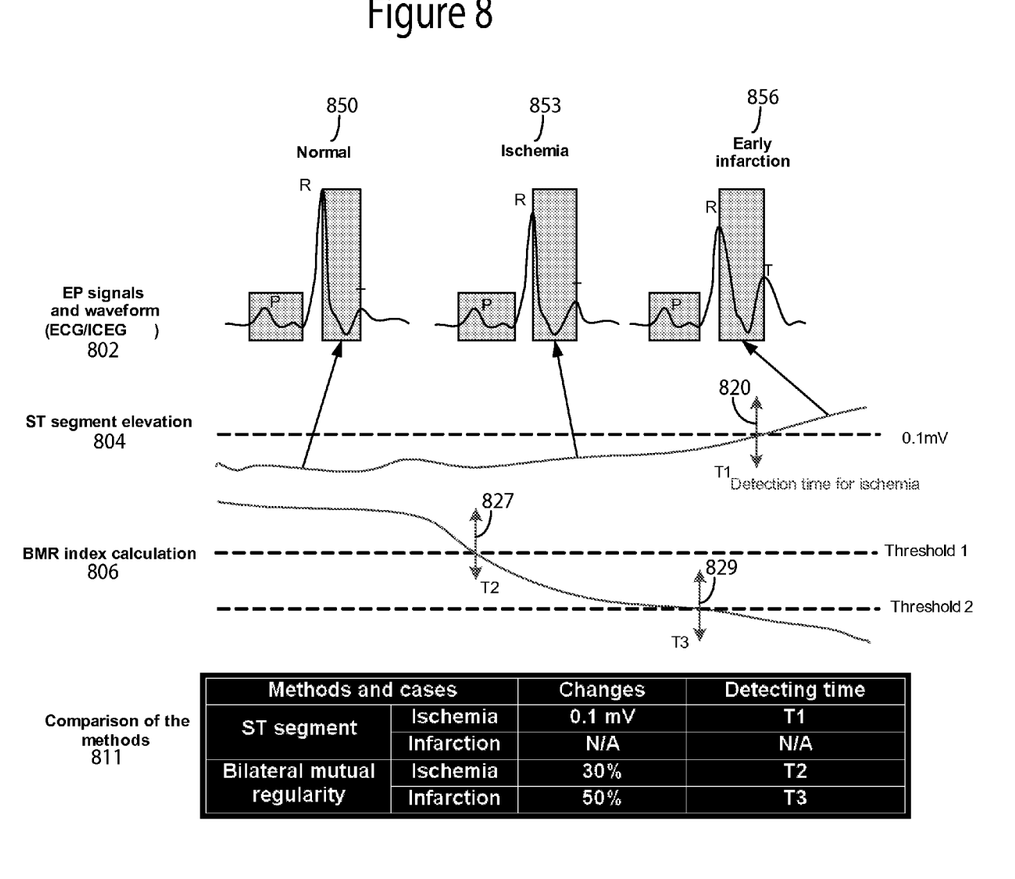
FIG. 8 shows simulation data and signals for myocardial ischemia detection using calculated bilateral mutual regularity values, according to invention principles.

FIG. 8 shows simulated ECG data and signals showing myocardial ischemia detection using calculated bilateral mutual regularity values. FIG. 8 shows Lead II surface ECG data 802 having normal 850, ischemia 853 and early infarction 856 rhythms and compares a known standard for myocardial ischemia detection (based on ST segment elevation) and bilateral mutual regularity calculation and shows that this calculation improves results. A bilateral mutual regularity continuously calculated value 806 is compared with an ST segment measurement 804 (the shift window size for the mutual regularity calculation is 5 heart beats). Calculated bilateral mutual regularity 806 values for normal 850, ischemia 853 and early infarction 856 beats are 88.3, 56.5 and 34.6 respectively. Ischemia is detected by ST segment elevation exceeding 0.1 mv at time T1 820 and is advantageously detected earlier by calculated bilateral mutual regularity value exceeding a 30% change threshold at time T2 827. Infarction is detected by the calculated bilateral mutual regularity value exceeding a 50% change threshold at time T3 829. Thresholds used by the different detection methods are summarized in Table 811.

System 10 (FIG. 1) adaptively selects a bilateral mutual regularity threshold value for cardiac condition detection in response to patient demographic data (age, weight, height, gender) and clinical condition being detected or procedure being performed. For ischemia event detection, a bilateral mutual regularity value shows early detection time (T1–T2>30 seconds, T1–T3>5 seconds) and a bilateral mutual regularity value also indicates severity. A 50% change in value may be used for early infarction detection, for example, and provides earlier ventricular myocardial ischemia event diagnosis. A bilateral mutual regularity value calculation may be used for different kinds of medical signal, such as temperature, energy and blood pressure signals, for example. Further, prior knowledge of medical signal characteristics facilitates statistical bilateral mutual regularity calculation and adaptive dynamic determination of a cardiac condition detection threshold.

Figure 9:
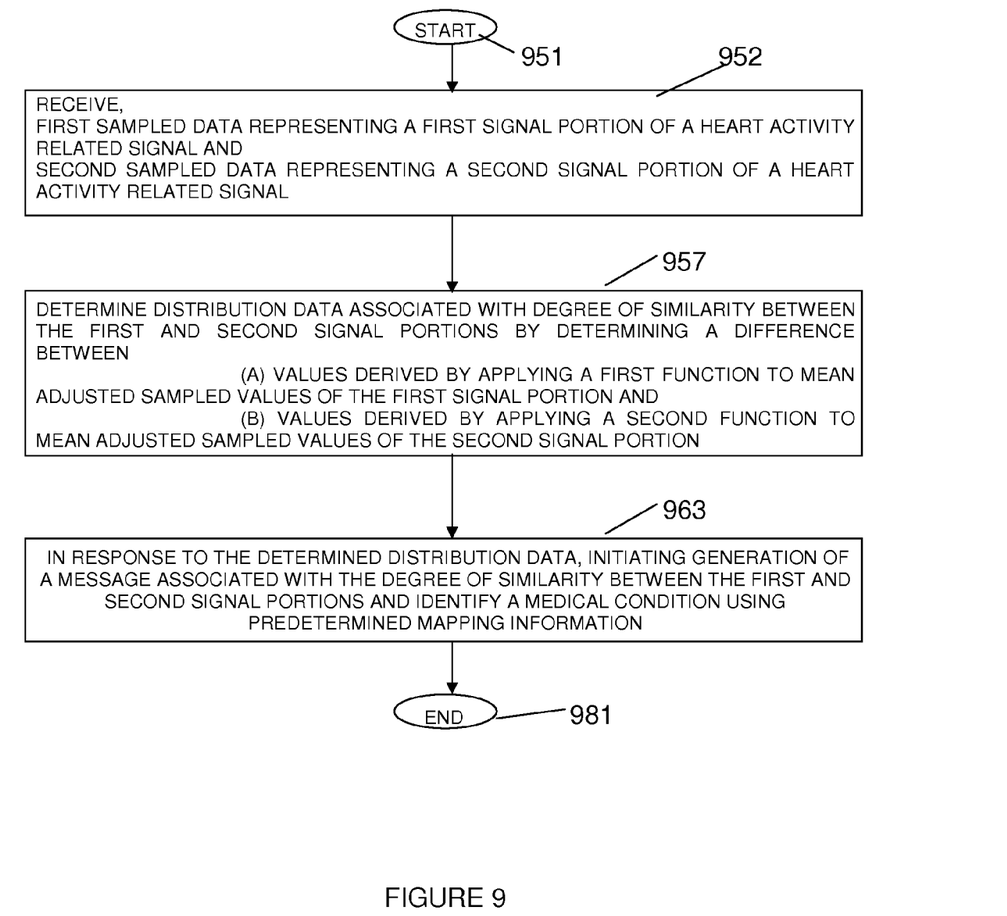
FIG. 9 shows a flowchart of a process used by a system for heart performance characterization and abnormality detection, according to invention principles.

FIG. 9 shows a flowchart of a process used by system 10 (FIG. 1) for heart performance characterization and abnormality detection. In step 952 following the start at step 951, input processor 12 receives, first sampled data representing a first signal portion of a heart activity related signal and second sampled data representing a second signal portion of a heart activity related signal. In step 957, signal processor 15, determines distribution data associated with degree of similarity between the first and second signal portions by determining a difference between (a) values derived by applying a first function to mean adjusted sampled values of the first signal portion and (b) values derived by applying a second function to mean adjusted sampled values of the second signal portion. In different embodiments, the first function and the second function comprise probability density functions, Gaussian functions, frequency spectrum functions or statistical functions. Further, the mean adjusted sampled values of the first signal portion are derived by taking a difference between individual sampled values and an average of sampled values, substantially in the first signal portion and the mean adjusted sampled values of the second signal portion are derived by taking a difference between individual sampled values and an average of sampled values, substantially in the second signal portion.

In one embodiment, signal processor 15 determines the distribution data using a function of the form, $$p_{RT\text{-}P}(x) = p_{RT}(x-\mu_{RT}) - p_P(x-\mu_P)$$

where, x is a data point in the distribution, p(•) is a distribution probability function, $p_{RT}(•)$ and $p_P(•)$ are a statistical distribution for an RT portion and P portion of a signal respectively and $\mu_{RT}$ and $\mu_P$ are the mean value of the RT and P wave signal portions sampled data. In a further embodiment, signal processor 15 derives a regularity value by summing multiple values individually comprising a product of a determined distribution data value and a logarithm of the determined distribution data value. Signal processor 15 derives the regularity value using a function of the form, $$\frac{|\mu_{RT} - \mu_P|}{|\delta_{RT} - \delta_P|} \cdot \left[ -\sum_{x \in \Omega} p_{RT\text{-}P}(x) \cdot \log p_{RT\text{-}P}(x) \right]$$

where $\mu_{RT}$ and $\mu_P$ are the mean value of the RT and P wave signal portions, $\delta_{RT}$ and $\delta_P$ are standard deviations of the RT and P wave signal portions; $p_{RT\text{-}P}(x)$ is the calculated distribution data; $\Omega$ is the data space of the mutual distribution for an atrial and ventricular combined statistical distribution signal.

In response to the determined distribution data in step 963, processor 15 initiates generation of a message associated with the degree of similarity between the first and second signal portions. Signal processor 15 uses predetermined mapping information, associating ranges and threshold values of the distribution data or values derived from the distribution data with corresponding medical conditions, and compares the distribution data or values derived from the distribution data, with the ranges and thresholds and generates an alert message indicating a potential medical condition. The predetermined mapping information associates ranges and thresholds of the distribution data or values derived from the distribution data with particular patient demographic characteristics and with corresponding medical conditions and signal processor 15 uses patient demographic data including at least one of, age weight, gender and height in comparing the distribution data or values derived from the distribution data with the ranges and thresholds and generating an alert message indicating a potential medical condition. The process of FIG. 9 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system analyzes cardiac electrophysiological signals using mutual signal regularity to detect and characterize cardiac arrhythmia and heart tissue functions. Further, the processes and applications may, in alternative embodiments, be located on one or more (e.g., distributed) processing devices on a network linking the units of FIG. 1. Any of the functions and steps provided in FIGS. 1-9 may be implemented in hardware, software or a combination of both.

What is claimed is:

1. A system for heart performance characterization and abnormality detection, comprising:
   an input processor for receiving,
      first sampled data representing a first signal portion of a heart electrical activity related signal and
      second sampled data representing a second signal portion different to said first signal portion of the heart electrical activity related signal; and
   a signal processor for,
      determining distribution data associated with degree of similarity between the first and second signal portions by determining a difference between
         (a) values derived by applying a first function to mean adjusted sampled values of the first signal portion and
         (b) values derived by applying a second function to mean adjusted sampled values of the second signal portion and
      in response to the distribution data, initiating generation of a message associated with said degree of similarity between the first and second signal portions;
   wherein said signal processor derives a regularity value by summing a plurality of values individually comprising a product of a determined distribution data value and a logarithm of said distribution data value.

2. A system according to claim 1, wherein
said first function and said second function comprise probability density functions.

3. A system according to claim 1, wherein
said mean adjusted sampled values of the first signal portion are derived by taking a difference between individual sampled values of said first signal portion and an average of said sampled values of said first signal portion and
said mean adjusted sampled values of the second signal portion are derived by taking a difference between individual sampled values of said second signal portion and an average of said sampled values of said second signal portion.

4. A system according to claim 1, wherein
said first function and said second function comprise Gaussian functions.

5. A system according to claim 1, wherein
said first function and said second function comprise at least one of, (a) frequency spectrum functions and (b) statistical functions.

6. A system according to claim 1, wherein
said signal processor determines said distribution data using a function of a form, $$p_{RT\_P}(x) = p_{RT}(x - \mu_{RT}) - p_P(x - \mu_P)$$

where, x is a data point in a distribution, $p(\bullet)$ is a distribution probability function, $p_{RT}(\bullet)$ and $p_P(\bullet)$ are a statistical distribution for an RT portion and P wave portion of a signal respectively and $\mu_{RT}$ and $\mu_p$ are mean values of the RT portion and P wave portion sampled data, respectively.

7. A system according to claim 1, wherein said signal processor derives said regularity value using a function of a form, $$\frac{|\mu_{RT} - \mu_P|}{|\delta_{RT} - \delta_P|} \cdot \left[ -\sum_{x \in \Omega} p_{RT-P}(x) \cdot \log p_{RT-P}(x) \right]$$

where $\mu_{RT}$ and $\mu_p$ are a mean value of RT and P wave signal portions, $\delta_{RT}$ and $\delta_P$ are standard deviations of the RT and P wave signal portions; $p_{RT-P}(x)$ is calculated distribution data; $\Omega$ is data space of the mutual distribution for an atrial and ventricular combined statistical distribution signal.

8. A system according to claim 1, wherein said signal processor uses predetermined mapping information, associating ranges of said distribution data or values derived from said distribution data with corresponding medical conditions, and compares said distribution data or values derived from said distribution data, with said ranges and generates an alert message indicating a potential medical condition.

9. A system according to claim 8, wherein said predetermined mapping information associates ranges of said distribution data or values derived from said distribution data with particular patient demographic characteristics and with corresponding medical conditions and said signal processor uses patient demographic data including at least one of, age, weight, gender and height in comparing said distribution data or values derived from said distribution data with said ranges and generating the alert message indicating the potential medical condition.

10. A system according to claim 1, wherein said signal processor uses predetermined mapping information, associating a threshold value with said distribution data or values derived from said distribution data with corresponding medical conditions, and compares said distribution data or values derived from said distribution data, with said threshold value and generates an alert message indicating a potential medical condition.

11. A method for heart performance characterization and abnormality detection, comprising the steps of:
receiving,
first sampled data representing a first signal portion of a heart electrical activity related signal and
second sampled data representing a second signal portion of the heart electrical activity related signal; and
determining distribution data associated with degree of similarity between the first and second signal portions by determining a difference between
(a) values derived by applying a first function to mean adjusted sampled values of the first signal portion and
(b) values derived by applying a second function to mean adjusted sampled values of the second signal portion and in response to the distribution data, initiating generation of a message associated with said degree of similarity between the first and second signal portions; and deriving a regularity value by summing a plurality of values individually comprising a product of a determined distribution data value and a logarithm of said distribution data value.

12. A method according to claim 11, wherein said first function and said second function comprise probability density functions.

13. A method according to claim 11, wherein said mean adjusted sampled values of the first signal portion are derived by taking a difference between individual sampled values of said first signal portion and an average of said sampled values of said first signal portion and
said mean adjusted sampled values of the second signal portion are derived by taking a difference between individual sampled values of said second signal portion and an average of said sampled values of said second signal portion.

14. A method according to claim 11, wherein said first function and said second function comprise Gaussian functions.

15. A method according to claim 11, wherein said first function and said second function comprise a same function.

16. A system according to claim 1, wherein said first function and said second function comprise a same function.

17. A system according to claim 1, wherein said first signal portion and said second signal portion are in a single heart cycle.

18. A method according to claim 11, wherein said first signal portion and said second signal portion are associated with atrial and ventricular repolarization procedures, respectively.

19. A system according to claim 1, wherein said heart electrical activity related signal comprises at least one of an electro-cardiogram (ECG) signal and an intra-cardiac electrogram (ICEG) signal.

* * * * *